US00PP12702P2

(12) United States Plant Patent
Vandenberg

(10) Patent No.: US PP12,702 P2
(45) Date of Patent: Jun. 11, 2002

(54) CHRYSANTHEMUM PLANT NAMED 'ORANGE PILAR'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/756,362

(22) Filed: Jan. 9, 2001

(51) Int. Cl.[7] ..... A01H 5/00
(52) U.S. Cl. ..... Plt./296
(58) Field of Search ..... Plt./286, 290, 295, Plt./296

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric. Biol., 22(3–4): 138–142.*

Broertjes et al., 1980, "A mutant of mutant of a . . . Irradiation of progressive radiation induced mutants in a mutation breeding programme with *Chrysanthemum morifolium*", Ephytica, 29:525–530.*

Gosling, ed., 1979 "The Chrysanthemum Manual—6$^{th}$ edition", The National Chrysanthemum Society, London, Essex Telegraph Press, Ltd., pp. 329–336.*

Broertjes, et al. 1978, "Application of Mutation Breeding Methods In the Improvement of Vegetatively Propagated Crops", Elsevier Sci. Pub. Co., New York, pp. 162–175.*

Searle, et al., 1968, "Chrysanthemums The Year Round," Blanford Press, London, pp. 27–29, 320–327.*

Chan, 1966, "Chrysanthemum and rose mutations induced by x–rays", Am. Soc. Hort. Sci. Proc., pp. 613–620.*

Broertjes, 1966, "Mutation breeding of chrysanthemums", Euphytica, 15:156–162.*

Dowrick, et al., 1966, "The induction of mutations in chrysanthemum using x– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Orange Pilar', characterized by its anemone-type inflorescences that are about 6.4 cm in diameter and with large anemone centers; attractive soft orange ray florets and bright yellow disc florets; freely and early flowering habit; dark green foliage; thick and strong stems; long peduncles; and good postproduction longevity with inflorescences maintaining good substance and color for about three or four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Orange Pilar'.

The new Chrysanthemum is a product of a mutation induction breeding program conducted by the Inventor in Salinas, Calif. The objective of the program is to create new Chrysanthemum cultivars with desirable inflorescence form and floret colors, good substance, and good postproduction longevity.

The new Chrysanthemum is a naturally-occurring whole plant mutation of a proprietary induced mutation that originated by exposing unrooted cuttings of the Chrysanthemum cultivar Pilar, disclosed in U.S. Plant Pat. No. 10,331, to X-ray radiation. The new Chrysanthemum was discovered and selected by the Inventor as a single flowering plant within a population of plants of the irradiated selection in May, 1996 in Salinas, Calif. The selection of this plant was based on its desirable inflorescence form and floret colors and good postproduction longevity.

Asexual reproduction of the new Chrysanthemum by terminal cuttings taken in a controlled environment in Salinas, Calif., has shown that the unique features of this new Chrysanthemum are stable and reproduced true to type in successive generations.

SUMMARY OF THE INVENTION

The cultivar Orange Pilar has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Orange Pilar'. These characteristics in combination distinguish 'Orange Pilar' as a new and distinct cultivar:

1. Anemone-type inflorescences that are about 6.4 cm in diameter and with large anemone centers.
2. Attractive soft orange ray florets and bright yellow disc florets.
3. Very freely flowering habit with numerous inflorescences per stem.
4. Early flowering, response time is about 49 days.
5. Dark green foliage.
6. Thick and strong stems.

7. Long peduncles.
8. Good postproduction longevity with inflorescences maintaining good substance and color for about three or four weeks in an interior environment.

Plants of the new Chrysanthemum differ from plants of the cultivar Bronze Pilar, disclosed in U.S. Plant Pat. No. 10,760, primarily in ray floret color as plants of the cultivar Bronze Pilar have bronze-colored ray florets. Plants of the new Chrysanthemum also differ from plants of the cultivar Pilar, primarily in ray floret color as plants of the cultivar Pilar have purple-colored ray florets.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Orange Pilar' grown as a spray-type cut Chrysanthemum.

The photograph on the second sheet comprises a close-up view of typical inflorescences of 'Orange Pilar'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on May 30, 2000 and received 20 long day/short nights followed by short day/long nights until flowering. Plants were grown as single-stem cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Aug. 21, 2000.

Botanical classification: *Chrysanthemum×morifolium* cultivar Orange Pilar.

Commercial classification: Anemone spray-type cut Chrysanthemum.

Parentage: Naturally-occurring whole plant mutation of a proprietary *Chrysanthemum×morifolium* induced mutation, not patented.

Propagation:

*Type.*—Terminal tip cuttings.

*Time to rooting.*—Seven to ten days with soil temperatures of 21° C.

*Root description.*—Fine, fibrous and well-branched.

Plant description:

*Appearance.*—Herbaceous anemone spray-type cut flower.

*Flowering stem description.*—Aspect: Erect. Strength: Strong. Length: About 88.9 cm. Diameter: About 7.5 mm. Texture: Pubescent; fine, white. Color: 146A.

*Foliage description.*—Arrangement: Alternate. Length: About 11.2 cm. Width: About 8 cm. Apex: Cuspidate to mucronate. Base: Mostly truncate. Margin: Palmately lobed; sinuses parallel to convergent and overlapping. Texture: Upper and lower surfaces pubescent. Veins prominent on lower surface. Color: Young foliage upper surface: Darker than 147A. Young foliage lower surface: Close to 147A. Mature foliage upper surface: 147A; venation, 147A to 147B. Mature foliage lower surface: Close to 147B; venation, close to 146C. Petiole: Length: About 2.5 cm. Diameter: About 3 mm. Color: Upper surface: 146B to 146C. Lower surface: 146C.

Flowering description:

*Appearance.*—Anemone spray-type inflorescence form with elongated oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 49 days later.

*Postproduction longevity.*—In an interior environment, flowering stems will maintain good color and substance for about three or four weeks in an interior environment after one week of cool storage.

*Quantity of inflorescences.*—Freely flowering with about 13 inflorescences per flowering stem.

*Inflorescence size.*—Diameter: About 6.4 cm. Depth (height): About 1.8 cm. Diameter of disc: About 3.2 cm. Diameter of receptacle: About 8.5 mm.

*Ray florets.*—Shape: Elongated oblong. Length: About 3.2 cm. Width: About 8.5 mm. Corolla tube length: About 5 mm. Corolla tube diameter: About 1 mm. Apex: Mostly acute. Base: Attenuate. Margin: Entire. Texture: Satiny, smooth, glabrous; longitudinally ridged. Aspect: Concave to flat. Aspect: Initially upright; when mature, about 90° from vertical. Number of ray florets per inflorescence: About 90 arranged in about four rows. Color: When opening, upper surface: Ground color, 9A, faintly overlain with 45A to 46A; overall tonality, close to 163A to 163B with reddish overtones. When opening, lower surface: Ground color, 9A to 9B, very faintly underlain with 53A to 59A; overall tonality, 162A to 11A. Mature, upper surface: Ground color, 9A, faintly overlain with 45A to 46A; overall tonality, 163A to 163B with reddish overtones. Mature, lower surface: Ground color, 9A to 9B, very faintly underlain with 53A to 59A; overall tonality, 162A to 162B to 11A.

*Disc florets.*—Shape: Enlarged tubular; flared. Length: About 1.5 cm. Width: Apex: About 5 mm. Base: About 1 mm. Number of disc florets per inflorescence: Numerous, typically about 169. Color: Immature: 144A to 145A to 154A. Mature, tube: Apex and mid-section: 9A. Base: 155D. Mature, throat: Apex and mid-section: 9A faintly overlain with 45A to 46A. Base: 9A.

*Peduncle.*—Aspect: Angled about 35° from vertical. Strength: Strong, flexible. Length: First peduncle: About 8.75 cm. Fourth peduncle: About 10.75 cm. Seventh peduncle: About 13.4 cm. Diameter: About 2.5 mm. Texture: Very fine pubescence. Color: 146A.

*Reproductive organs.*—Androecium: Present on disc florets only. Anther color: 9A. Amount of pollen: Scarce. Pollen color: 9A. Gynoecium: Present on both ray and disc florets.

*Seed.*—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures lower than 40° C.

It is claimed:

1. A new and distinct cultivar of Chrysanthemum plant named 'Orange Pilar', as illustrated and described.

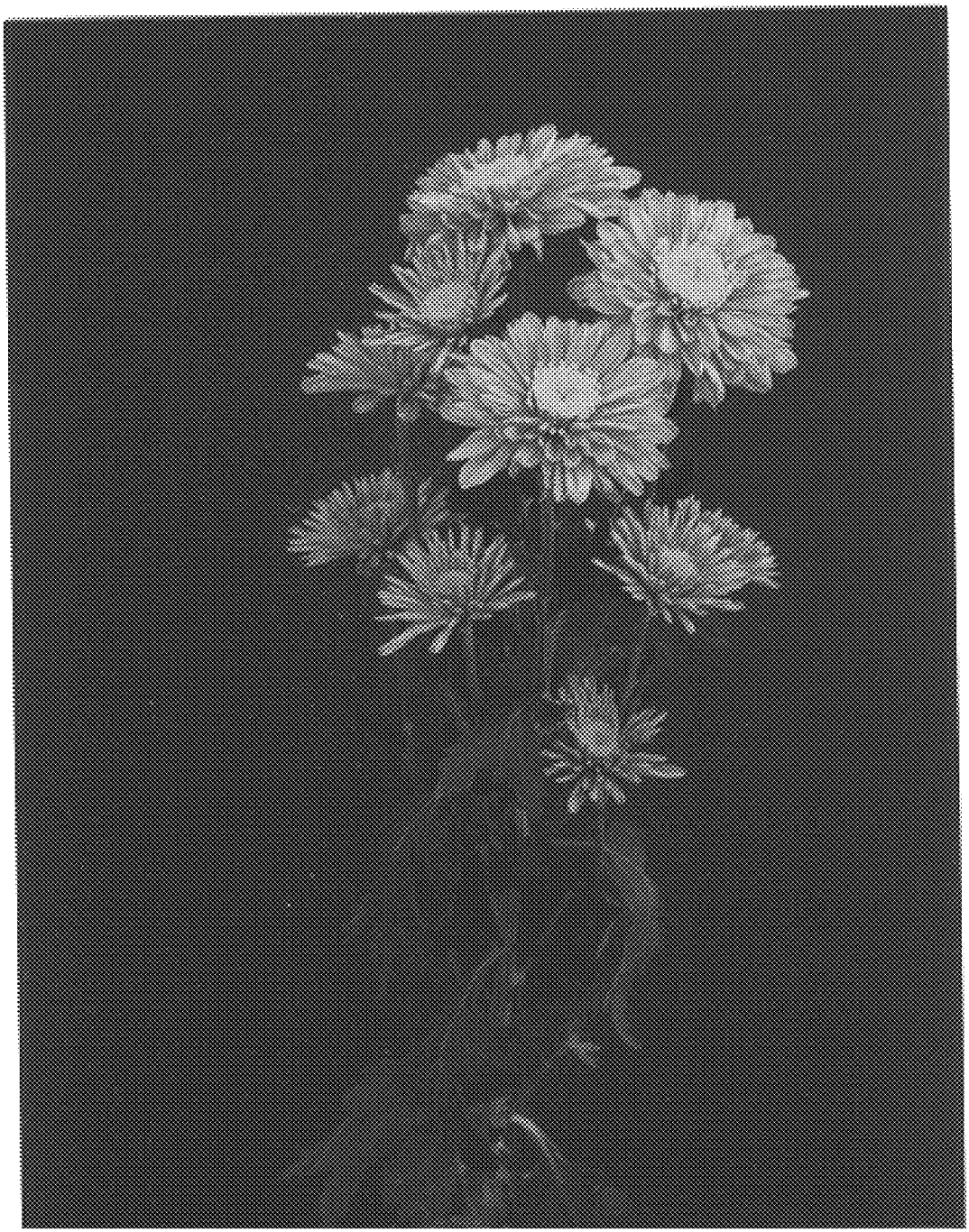

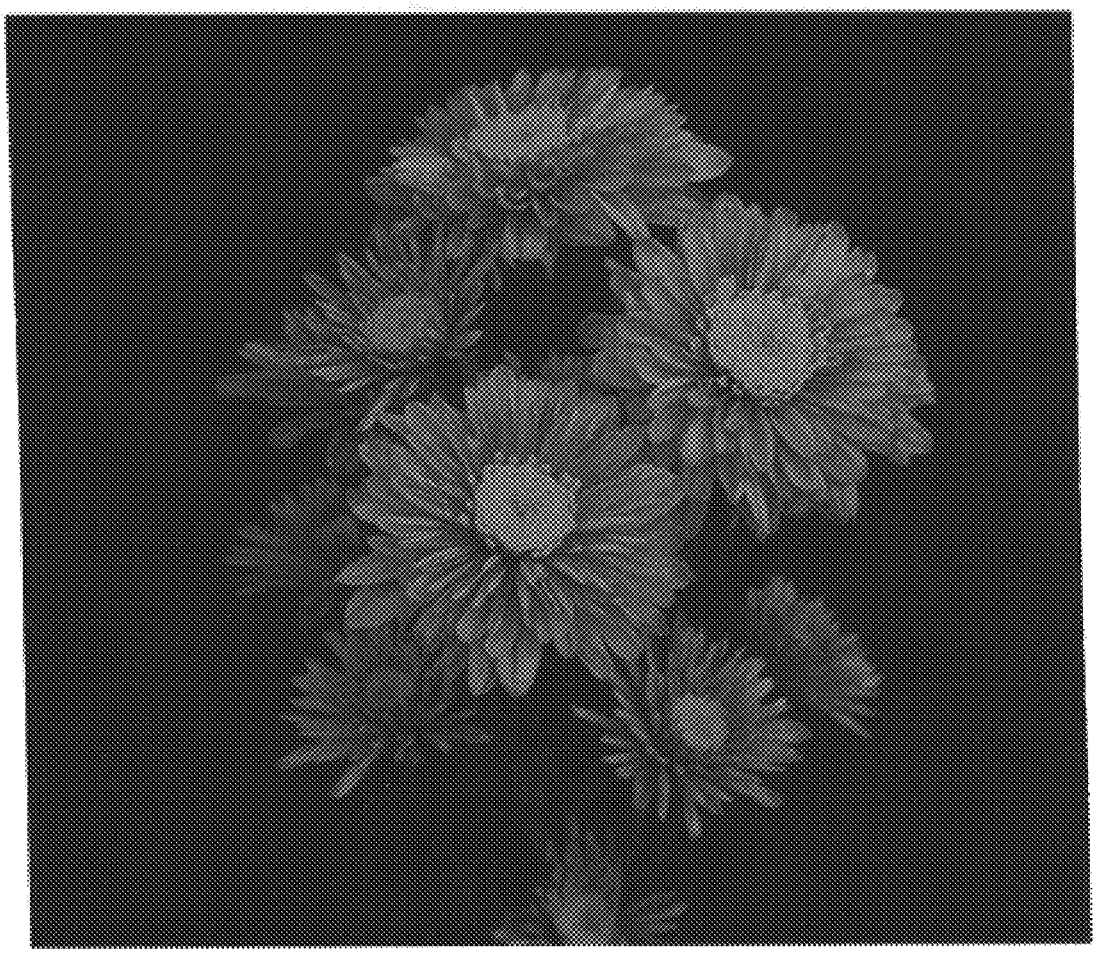

* * * * *